United States Patent [19]

Bertini Curri et al.

[11] Patent Number: 5,176,919
[45] Date of Patent: Jan. 5, 1993

[54] PHARMACEUTICAL COMPOSITIONS HAVING ACTIVITY ON THE CUTANEOUS MICROCIRCULATION

[75] Inventors: Sergio Bertini Curri; Ezio Bombardelli, both of Milan, Italy

[73] Assignee: Indena, S.p.A., Milan, Italy

[21] Appl. No.: 585,731

[22] Filed: Sep. 20, 1990

[30] Foreign Application Priority Data

Sep. 21, 1989 [IT] Italy ................ 21786 A/89

[51] Int. Cl.⁵ .............................. A61K 37/22
[52] U.S. Cl. .................... 424/450; 514/455; 514/887; 549/387
[58] Field of Search ............ 424/450; 514/887, 455; 549/387

[56] References Cited

U.S. PATENT DOCUMENTS

| | | | |
|---|---|---|---|
| 4,169,204 | 9/1979 | Hearst et al. | 546/270 |
| 4,284,569 | 8/1981 | Gammill | 260/345.2 |
| 4,304,722 | 12/1981 | Gammill | 549/387 X |
| 4,313,881 | 2/1982 | Gammill | 549/387 |
| 4,313,882 | 2/1982 | Gammill | 549/387 |
| 4,313,883 | 2/1982 | Gammill | 549/387 |
| 4,399,146 | 8/1983 | Schurr et al. | 424/283 |
| 4,412,071 | 10/1983 | Gammill | 544/58.6 |
| 4,434,295 | 2/1984 | Gammill | 549/344 |
| 4,438,274 | 3/1984 | Gammill | 549/387 |
| 4,454,152 | 6/1984 | Barry et al. | 424/283 |
| 4,540,798 | 9/1985 | Gammill | 549/387 |
| 4,542,228 | 9/1985 | Gammill | 549/387 |
| 4,937,078 | 6/1990 | Mezei et al. | 424/456 |

*Primary Examiner*—Thurman K. Page
*Assistant Examiner*—William E. Benston, Jr.
*Attorney, Agent, or Firm*—Mathews, Woodbridge & Collins

[57] ABSTRACT

Pharmaceutical and cosmetic compositions comprising extracts of Ammi visnaga and Ammi majus or the vasoactive agents contained therein are described.

10 Claims, No Drawings

PHARMACEUTICAL COMPOSITIONS HAVING ACTIVITY ON THE CUTANEOUS MICROCIRCULATION

The present invention concerns pharmaceutical and cosmetic compositions comprising extracts of Ammi visnaga and Ammi majus or the vasoactive agents contained therein, particularly visnadine, kelline and other coumarins and flavoncoumarols. The compositions of the invention are useful for the topical, epicutaneous treatment of pathological or paraphysiological conditions of the skin and of the adnexa thereof, characterized by functional or organic deficiencies of the local microcirculation associated with ischemia, stasis and trophic disturbances secondary to impaired microvascular-tissue relationships.

The therapeutic use of extracts of Ammi visnaga and Ammi majus or of active constituents thereof is already known, particularly in the cardiological field for the treatment of ischemic cardiopathies, namely of anginous attacks and of chronic-degenerative myocardial diseases. More recently, it has been reported that some dihydropyranocoumarins and dihydrofuranocoumarins are endowed with platelet anti-aggregant activity similar to that of dipyridamol; this could lead to their therapeutic uses as anti-thrombotic agents and cyclic AMP-phosphodiesterase inhibitors. Some derivatives of visnaginone and of kellinone were reported to be endowed with antibacterial and anti-helmintic activity. High oral doses of visnadine have been used by BENSIMON (G.M. de France, Tome 77, No. 29, 1970, 6269–6275) and by GOURNAY (G.M. de France, Tome 78, No. 3, 1971, 390–391) in the treatment of peripheral arteriopathies affecting large arterial vessels.

The results of said studies show that: the compound is not convenient to use, it asks for high daily doses, it must be administered for prolonged periods and produces favourable responses in an unsatisfactorily low proportion of patients. Moreover, the administration of these high dosages for long periods is associated with remarkable side-effects, especially gastric disturbances, insomnia and paresthesiae which may even require discontinuation of the therapy.

The available knowledge refers only to the treatment of disorders affecting large arteries and of pathological conditions of peripheral vascular diseases secondary to occlusion of large arterial vessels, without any mention of a possible effect of the compound on the microcirculation and on the smallest arterial/arteriolar vessels at precapillary level, with particular reference to the cutaneous circulation.

It has now been found according to the present invention that the extracts of Ammi visnaga and Ammi majus containing visnadine and/or coumarins as well as visnadine-like flavoncoumarols and visnadine itself in purified form, have the following properties:

a) they are not "vasodilators" and therefore they do not inhibit the tonus and the sphygmic activity of the muscular media in medium-sized or large arteries. By contrast, they exert a marked stimulatory effect on microvascular motility and on the sphygmic activity of the smooth muscle constituents of the media of small arteries and precapillary arterioles. The supposed "vasodilator effect" is only a consequence of substantial modifications in the microcirculatory haemodynamics;

b) their biological effect is therefore mainly at microcirculatory level. These agents act in fact on small arteries and precapillary arterioles and determine as an immediate haemodynamic consequence increase of the volume and of the blood flow-rate in capillary network: the tissue oxygenation increases and the trophic exchanges are enhanced;

c) they are highly effective in antagonizing the vasal spasm induced by cold, particularly in the circulation of the fingertip.

The invention refers therefore to pharmaceutical and cosmetic compositions comprising extracts of Ammi visnaga and Ammi majus containing visnadine and/or visnadine-like coumarins and flavoncoumarols, or visnadine itself in purified form, for the therapeutic treatment by the topical epicutaneous route of peripheral vascular acrosyndromes, particularly of Raynaud's disease and of local perfusion deficiencies of the upper and lower limbs, and for the cosmetic treatment of defects due to insufficient blood perfusion of the skin and of the subcutaneous adipose tissue, particularly for the treatment of precocious senile involution of the face and neck skin, cellulitis, cutaneous stretch marks, alopecias and similar conditions.

The epicutaneous administration is not only surprisingly more active and effective but it is also practically devoid of side-effects such as those described for the oral administration of high doses.

The active and effective doses by topical epicutaneous route are by far lower, up to 50 times, than that used for the oral route and the time necessary for the onset of the biological effect, which may be measured by means of instrumental methods, is of some hours whereas the oral route asks for days or months.

The pharmaceutical or cosmetic compositions of the invention may be prepared using known methods and excipients, such as those disclosed in "Remington's Pharmaceutical Sciences Handbook" Mack Pub. Co., NY, USA.

Examples of suitable formulations include creams, ointments, gel, lotions containing from 1 to 5% of visnadine or the equivalent of extracts or of visnadine-like compounds (visnaginone, kelline, kellinone, coumarins, dihydropyranocoumarins or dihydrofuranocoumarins derived from plants of the Ammi genus).

These formulations may be applied on the skin so as to cover the area to be treated once or more times a day.

It is particularly preferred to use a carrier suited for the absorption through the epidermal barrier. Liposomal carriers obtainable from lecithins, unsaturated or saturated phosphatidylcholine or other conventional phospholipids are particularly preferred.

The Ammi extracts may be obtained according to known methods, such as those disclosed in the following Examples wherein specific reference is made to visnadine. It is however apparent that all the above cited extracts containing visnadine or the above cited visnadine-like compounds contained in plants of the Ammi genus may be used in substitution of or in combination with visnadine, in any quantitative ratio.

EXAMPLE 1

Extemporaneous preparation of an aqueous microdispersion of visnadine with pure soy-bean phosphatidylcholine 100 g of visnadine are dissolved together with 400 g of pure soy-bean phosphatidylcholine in 1 l of methylene chloride; the solvent is evaporated under vacuum and the syrupy residue is dispersed in 5 l of water in a high speed turboemulsifier under strong stirring for 5 h; 200 g of mannitol are then added and the mixture is distributed in 10 ml vials and lyophilized. This lyophilized material, suspended in 5 ml of water, is directly applied on the cutis to be treated.

EXAMPLE 2

Preparation of an Ammi visnaga extract with high visnadine titer.

100 Kg of finely ground blossoming tops of the plant are placed in a 400 l extractor suited for the use of gases in hypercritic conditions; the plant material is extracted with carbon dioxide for 1 h at 35° C. and under a pressure of 100 bar to remove the undesired fatty substances; after elimination of the extract from the condenser, the extraction with carbon dioxide is continued at 45° C. and 180 bar for 3 h or until complete extraction of visnadine from the plant material. The obtained extract (3.4 kg) may be directly used or it may be subjected to purification by partition between immiscible solvents according to the methods of Example 3.

EXAMPLE 3

Preparation of visnadine from lipophilic extracts containing it obtained according to Example 2

2.5 Kg of lipophilic extract prepared according to Example 2 are dissolved in 25 l of 95% aqueous methanol and thoroughly extracted with 20 l of n-hexane until complete extraction of the extractable undesired material; the pooled hexane extracts are counter-washed with 5 l of 95% methanol which are added to the previous methanol phase. The methanol solution is concentrated under vacuum up 10 l and the concentrate is diluted with an equal volume of water; the obtained suspension is counter-extracted with n-hexane until complete extraction of visnadine. After addition of a 3% proportion of ethanol, the hexane solution is concentrated resulting in crystallization of the desired product which exhibits spectroscopic and physico-chemical characteristics equivalent to those described in literature.

EXAMPLE 4

Lotion for the treatment of hair scalp.

| 100 g of composition contain: | |
|---|---|
| Visnadine | 2 g |
| Soy-bean phosphatidylcholine (96%) | 4 g |
| Softigen ® 727 | 25 g |
| Volpo ® 20 | 7 g |
| Octylinone | 0.1 g |
| Imidazolidinylurea | 0.3 g |
| Purified water | q.s. to 100 g |

EXAMPLE 5

Gel containing as active principle a mixture of visnadine and kelline

| 100 g of gel contain: | |
|---|---|
| Visnadine | 1 g |
| Kelline | 0.5 g |
| Softigen ® 727 | 25 g |
| Volpo ® 20 | 7 g |
| Carbopol ® 934 | 1.5 g |
| Triethanolamine | 1 g |

| 100 g of gel contain: | |
|---|---|
| Imidazolidinylurea | 0.3 g |
| Purified water | q.s. to 100 g |

CLINICAL PHARMACOLOGY INVESTIGATIONS

Investigation A

The sphygmic activity of small arteries and arterioles of the subpapillary plexus and the cutaneous temperature of the fingertip were determined quantitatively in 30 healthy subjects (divided in two groups A and B) by using computerized infra-red photo-pulse plethysmography (i.r.Ph.P.P.) and direct cutaneous thermometry respectively. The same measurements were repeated at 15, 30, 45 and 60 minutes after the epicutaneous application of a visnadine formulation (prepared according to Example 1) in group A and placebo in group B. The application was always followed by a light massage until complete penetration of the product had been achieved.

As indicated by the data shown in Table 1, the preparation described in Example 1 induces a statistically significant increase in the arterial/arteriolar sphygmic activity as compared to baseline conditions. This, in turn, determines an increase in volume and velocity of the microcirculatory flow directed to the capillary networks located downstream, with consequent elevation of the cutaneous temperature without reddening and without active hyperemia. The placebo was found to be totally inactive.

TABLE 1

| Arterial/Arteriolar sphygmic activity | | | | | | |
|---|---|---|---|---|---|---|
| | Baseline | | | After treatment | | |
| Case n° | Second finger | Third finger | Fourth finger | Second finger | Third finger | Fourth finger |
| 1 | 56.81 | 112.33 | 88.12 | 218.25 | 111.25 | 135.50 |
| 2 | 152.00 | 77.68 | 34.40 | 269.33 | 182.00 | 138.80 |
| 3 | 178.50 | 146.20 | 114.50 | 54.33 | 141.75 | 116.00 |
| 4 | 23.40 | 16.75 | 32.00 | 31.16 | 46.75 | 110.00 |
| 5 | 59.90 | 31.20 | 40.00 | 105.10 | 120.00 | 100.60 |
| 6 | 50.80 | 34.30 | 17.25 | 76.50 | 164.50 | 133.60 |
| mean | 86.902 | 69.743 | 54.378 | 125.778 | 127.708* | 122.417* |
| +/− SD | 50.458 | 40.815 | 31.297 | 74.392 | 65.275 | 59.549 |

| Significance level (Baseline vs Q36) | | |
|---|---|---|
| 2° finger | t-Student = −0.963 N.S. | $p < 0.618$ |
| 3° finger | t-Student = −2.473 | $p < 0.056*$ |
| 4° finger | t-Student = −4.003 | $p < 0.011*$ |

| Cutaneous temperature | | | | | | |
|---|---|---|---|---|---|---|
| | Baseline | | | After treatment | | |
| Case n° | Second finger | Third finger | Fourth finger | Second finger | Third finger | Fourth finger |
| 1 | 30.590 | 30.290 | 27.910 | 30.230 | 30.490 | 31.560 |
| 2 | 30.450 | 31.870 | 26.000 | 31.200 | 31.530 | 32.570 |
| 3 | 30.300 | 32.830 | 26.900 | 30.904 | 32.220 | 32.950 |
| 4 | 27.300 | 24.970 | 26.830 | 32.520 | 31.500 | 34.210 |
| 5 | 26.180 | 24.300 | 24.460 | 32.560 | 31.440 | 34.590 |
| 6 | 25.740 | 24.010 | 23.300 | 32.840 | 32.050 | 34.990 |
| mean | 28.427 | 28.045 | 25.900 | 31.715* | 31.538 | 33.478* |
| +/− SD | 13.769 | 13.668 | 12.534 | 15.327 | 15.237 | 16.183 |

| Significance level (Baseline vs Q36) | | |
|---|---|---|
| 2° finger | t-Student = −2.438 | $p < 0.058*$ |
| 3° finger | t-Student = −2.068 N.S. | $p < 0.092$ |
| 4° finger | t-Student = −6.387 | $p < 0.002*$ |

These data indicate that, surprisingly, visnadine:

Acts selectively on the small arteries and arterioles of the cutaneous microcirculation;

Increases the volume of blood in the capillaries and opens to blood flow previously closed vessels in capillary networks. This results in increased cutaneous temperature and enhanced trophic exchanges even in normal, healthy subjects;

Is active by direct topical epicutaneous application to the desired site of action at dosages much lower than those used by the oral route.

In addition, the effects of topical epicutaneously applied visnadine are surprisingly more rapid and can be demonstrated readily by instrument-based measurements, as opposed to the situation observed after oral administration of doses at least 50-fold greater.

Investigation B

The arterial/arteriolar sphygmic activity of the fingertip and the cutaneous temperature under baseline conditions and after immersion of the right hand in an ice-water bath for 4 minutes ("cold test") were determined in healthy subjects divided into two groups (group A and group B) as in investigation A. The skin of the fingers and of the palmar and dorsal surface of the hand was treated with a visnadine preparation or with placebo as described in Example 1 and investigation A. Continuous computerized recordings of arterial/arteriolar sphygmic activity and of cutaneous temperature were made as in investigation A until all values had returned to baseline conditions, and the required time (in minutes) was calculated.

The results of this investigation clearly show that epicutaneous treatment with the preparation described in Example 1 causes a statistically significant reduction of the time required for flow conditions to return to baseline, while placebo treatment is without effect. These results demonstrate that visnadine:

After topical epicutaneous application, counteracts rapidly and effectively the vasoconstriction and the associated decrease in arterial/arteriolar sphygmic activity which follow exposure to cold ("cold test") in healthy subjects;

Potently antagonizes at microcirculatory level the cold-induced ischemia of the tissue;

May be used for the topical epicutaneous treatment of functional or organic peripheral vascular acrosyndromes due to microangiopathies and/or histangiopathies and characterized by hypoxic episodes affecting the extremities, secondary to abnormal cold-induced vasoconstriction and deficiency of the mechanisms regulating the local microcirculatory flow;

After topical epicutaneous application with an adequate vehicle, counteracts the physiological cold-induced vasoconstriction at very low doses.

Investigation C

Investigation C was performed in subjects with venous stasis and/or chronic venous insufficiency of the lower limbs and functional-anatomic alterations of the cutaneous arterial/arteriolar afferrents. The subjects were divided into two groups (group A and group B) as in investigation A. The filling time of the superficial venous plexus of the dorsum of the foot was recorded in these subjects by means of light reflectance rheography before and after 15 timed rhythmical flexion-extension movements of the foot. The profile of the resulting recording represents a mirror image of the venous pressure in the system. These measurements were repeated by using the same procedure after 3 weeks of epicutaneous treatment with a visnadine preparation of the type described in Example 1 or in Example 5. The preparation was applied twice daily over the entire surface of the lower limb, including the thigh. The experimental protocol was carried out according to a placebo-controlled, double-blind design. The arterial/arteriolar sphygmic activity of the subpapillary plexus of the supra-lateral region of the thigh was recorded in parallel by means of computerized infra-red plethysmography.

The results of this investigation indicate that the filling time of the superficial cutaneous venous plexus of the pretibial region is clearly prolonged in subjects treated with visnadine as compared to those treated with placebo, which is on the contrary without effect. Moreover, in visnadine-treated subject the sphygmic activity of the small arteries and arterioles of the subpapillary plexus of the supralateral region of the thigh increases by more than 50% compared to baseline conditions, with a clear-cut improvement in local microcirculatory flow. The subjects treated with the active preparation show an appreciable subjective improvement in the feeling of leg heaviness, paresthesiae and frequency of diurnal and nocturnal muscle cramps.

The instrument-based findings demonstrate that:

In the presence of capillaro-venular stasis causing a slowing and a pathological alteration of the microvascular-tissue exchanges, low dosages of topical epicutaneously applied visnadine are surprisingly effective in increasing the velocity and volume of the cutaneous microcirculatory flow, thus counteracting the blood stasis;

Topically applied visnadine is effective in reducing the microcirculatory stasis and the capillaro-venular dilation typically associated with stasis conditions and/or chronic venous insufficiency. Surprisingly, this activity is already observed at very low doses compared with those used by the oral route. The rapid onset of activity and the efficacy of this treatment can be documented by instrument-based observations and are statistically significant as compared to placebo.

Investigation D

Investigation D was performed in a group of male subjects with alopecia areata. The local microcirculatory conditions in the scalp area affected by the disease were evaluated by means of high-resolution contact thermometry and infra-red photo-plethysmography before and 60 minutes after the application of a hair lotion containing visnadine prepared according to Example 4.

The instrument-based findings demonstrate that:

Topical epicutaneous application of visnadine over the areas of alopecia is effective in increasing arterial/arteriolar sphygmic activity and cutaneous temperature. These effects are associated with an increase in volume/minute and velocity of microcirculatory flow, resulting in improved perfusion of the hair follicle;

Visnadine does not cause reddening secondary to cutaneous vasodilation, unlike other drugs or compounds which induce scalp hyperemia and reduce at the same time the volume of the local microcirculatory flow;

The vehicle (especially phospholipidic liposomes) exerts surprisingly an antiseborrheic action and reduces the lipid content of greasy hair. This allows a drastic reduction of the weekly frequency of the required hair washings;

The dose of visnadine which is active on the scalp microcirculation is much lower than those used orally for the vasodilating treatment of arterial diseases and/or coronary heart disease;

The action of the compound is exerted essentially by the topical route in the presence of an appropriate (preferably liposomal) vehicle.

Investigation E

Two groups of patients (group A and group B) with primary or secondary Raynaud's phenomenon were treated topically by epicutaneous application with an active preparation (prepared as described in Examples 1 and 5) or with placebo according to a double-blind design.

At baseline and after 30 days of treatment the patients were evaluated clinically and instrumentally by means of impedance plethysmography performed on the second, third and fourth finger of both hands.

The data obtained in this investigation indicate that the epicutaneous treatment with the active preparation induces an appreciable clinical improvement which was rated as "excellent" in 43% of the cases and "good" in 26% of the cases. The placebo preparation was found to be ineffective.

The instrument-based data indicate that the sphygmic waves of the arteries in the fingertip of treated fingers exhibit after treatment a statistically significant increase in amplitude as compared to placebo.

The clinical and instrument-based findings demonstrate that:

When applied topically over the extremities of limbs affected by pathological ischemic conditions or arterial-/arteriolar spasms causing capillary hypovolemia, visnadine induces a statistically significant improvement of clinical symptoms and instrument-based measurements. These effects are surprisingly already seen at dosages which are 30 to 50-fold lower than those used for the oral treatment of "arteritis", e.g. for their action at the level of large and medium sized arteries.

The vehicle used to facilitate the penetration across the epidermal barrier is preferably liposomal;

After topical "transepidermal" administration in pathological conditions (functional spasms of the microcirculation), visnadine exerts an hyperactivating action on the microcirculatory flow which is identical to that observed and documented in the "cold test" performed in healthy subjects (investigation B).

What is claimed is:

1. A topical composition for the treatment of insufficient peripheral perfusion comprising an amount of visnadine effective to treat insufficient peripheral perfusion in combination with a topically acceptable carrier.

2. The composition according to claim 1 wherein the carrier is a topically acceptable liposomal carrier.

3. The composition according to claim 2 wherein the liposomal carrier comprises a phospholipid.

4. The composition according to claim 3 wherein the phospholipid is a phosphatidylcholine.

5. The composition according to claim 1 wherein the composition is a cream, ointment, gel or lotion.

6. A method of treating insufficient peripheral perfusion comprising the topical application of a composition comprising an amount of visnadine effective to treat insufficient peripheral perfusion in combination with a topically acceptable carrier.

7. The method according to claim 6 wherein the carrier is a topically acceptable liposomal carrier.

8. The method according to claim 7 wherein the liposomal carrier comprises a phospholipid.

9. The method according to claim 8 wherein the phospholipid is a phosphatidylcholine.

10. The method according to claim 6 wherein the composition is a cream, ointment, gel or lotion.

* * * * *